United States Patent [19]

Engels et al.

[11] 4,430,262
[45] Feb. 7, 1984

[54] PREPARATION OF ISOCYANATES AND/OR DERIVATIVES THEREOF

[75] Inventors: Rainer Engels; Jan H. H. Meurs, both of Amsterdam, Netherlands

[73] Assignee: Shell Oil Company, Houston, Tex.

[21] Appl. No.: 357,011

[22] Filed: Mar. 11, 1982

[30] Foreign Application Priority Data

Jun. 5, 1981 [GB] United Kingdom ............... 8117258

[51] Int. Cl.³ ............... C07C 118/00; C07C 125/06; C07C 127/19
[52] U.S. Cl. .............................. 260/453 P; 204/59 R; 560/24; 560/25; 560/27; 560/29; 560/30; 560/31; 560/32; 560/157; 564/32; 564/48; 564/52; 564/53; 564/218
[58] Field of Search ............... 260/453 P; 560/24, 25, 560/27; 564/32, 48

[56] References Cited

U.S. PATENT DOCUMENTS 4,322,365  3/1982  Merger et al. ............... 260/453 P Primary Examiner—Dolph H. Torrence
Attorney, Agent, or Firm—Ronald R. Reper

[57] ABSTRACT

Isocyanates and derivatives thereof are prepared by oxidative conversion of compounds having at least one group

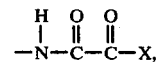

wherein X represents OY or

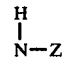

wherein Y is H, a metal ion or group $NR^3R^4R^5R^6$ wherein each of $R^3$, $R^4$, $R^5$ and $R^6$ which may be the same or different, is H, alkyl or (substituted) (alk)aryl and Z is a (substituted) alkyl or aryl group. Phenyl isocyanate and derivatives thereof are preferably prepared electrochemically from the corresponding oxamides and oxanilides.

11 Claims, No Drawings

PREPARATION OF ISOCYANATES AND/OR DERIVATIVES THEREOF

BACKGROUND OF THE INVENTION

The present invention relates to a process for the preparation of isocyanates and/or derivatives thereof. Isocyanates are compounds containing at least one group having the structure —N=C=O. They constitute very important starting materials for chemical processes, especially in the manufacture of polyurethanes which find wide application in the synthetic foam industry.

Isocyanates are normally prepared via the so-called "phosgene route": an appropriate amine is reacted with phosgene ($COCl_2$) to form the required isocyanate. That process, however, suffers from the severe drawback that phosgene is a chemical which is highly toxic.

Numerous attempts have been made over the years to find alternative routes for the preparation of isocyanates, especially the commercially interesting ones such as toluene diisocyanate (TDI) and methylene-4, 4'-diphenyldiisocyanate (MDI) via a "phosgene-free" route. Reference is made in this respect to "Recent Advances in Isocyanate Chemistry" by S. Ozaki (Chem. Rev. 72 (1972) 457–496). For instance, much emphasis has been laid on the reduction of aromatic nitro compounds with carbon monoxide in the presence of a lower alkanol and a selenium containing catalyst. The carbamates obtained can be converted easily into the corresponding isocyanates. However, a seemingly unavoidable disadvantage of that process is the presence of small but definite amounts of selenium (compounds) in the product so that even more research is devoted to solve the selenium problem.

Although isocyanates can be obtained under very severe reaction conditions (e.g., the dehydrogenative composition of formanilide and oxanilide at high temperatures, i.e., 750° C.–1000° C. under reduced pressure in the presence of a Pd/Ni MgO-catalyst (see Z. Chem., (1974), Part 5, page 192)) no general process has been suggested thus far which generates isocyanates and/or the corresponding carbamates under mild reaction conditions and which is not impaired by catalyst-removal problems.

It has now surprisingly been found that isocyanates and/or derivatives thereof can be obtained under mild reaction conditions and without substantial work-up problems by the oxidative conversion of starting materials possessing the structure —NH—CO—CO—X in the molecule. It is the interesting feature of the present invention that the choice of oxalic acid derivatives as starting materials in the process according to the present invention enables the use of simple and well-known oxidation techniques. Moreover, a great number of different oxalic acid derivatives can be used as starting materials.

SUMMARY OF THE INVENTION

The present invention thus relates to a process for the preparation of compounds containing at least one group having the structure —N=C=O and/or

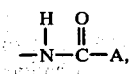

wherein A represents a group OB or $NR^1R^2$ wherein B represents an alkyl or aryl group which may or may not be substituted with one or more halogen atoms, alkyl or alkoxy groups and $R^1$ and $R^2$ which may be the same or different each represent a hydrogen atom or an alkyl or aryl group which may or may not be substituted with one or more halogen atoms, alkyl or alkoxy groups, which process comprises oxidatively converting in a reaction zone a compound having at least one group according to the structure

wherein X represents a group OY or

wherein Y represents a hydrogen atom, a metal ion or a group $NR^3R^4R^5R^6$ wherein each of $R^3$, $R^4$, $R^5$ and $R^6$ which may be the same or different, represent a hydrogen atom, an alkyl group having up to 8 carbon atoms, or an (alk)aryl group which may be substituted by one or more lower alkyl groups and Z represents an alkyl group or an aryl group which may be substituted by one or more substituents, and separating the conversion products from said reaction zone.

DESCRIPTION OF THE PREFERRED EMBODIMENTS

The present invention relates in particular to the oxidative conversion of compounds according to the general formula

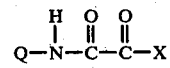

wherein X is as defined hereinbefore and Q represents an alkyl group or an aryl group which may contain one or more substituents.

Classes of compounds which can be converted oxidatively into isocyanates and/or the corresponding carbamates comprise alkyl, aryl, alkaryl and aralkyloxamic acids and salts thereof. Examples of alkyloxamic acids which can be used as starting materials comprise alkyloxamic acids having up to 12 carbon atoms in the alkyl group such as n-butyloxamic acid, t-butyloxamic acid, hexyloxamic acid and dodecyloxamic acid. Examples of aryloxamic acids comprise compounds according to the general formula

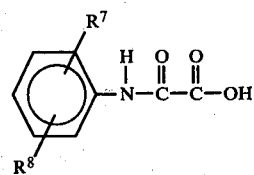

wherein $R^7$ and $R^8$ which may be the same or different each represent a hydrogen or halogen atom or an alkyl or alkoxy group, a group

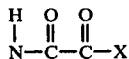

wherein X is as defined hereinbefore or a group

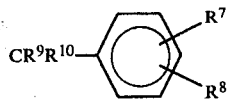

wherein $R^9$ and $R^{10}$ which may be the same or different each represent a hydrogen atom or an alkyl group.

Suitable salts comprise the alkali and alkaline earth metal salts and, preferably, the ammonium salts wherein the ammonium moiety can be represented by the group $NR^3R^4R^5R^6$ wherein $R^3$, $R^4$, $R^5$ and $R^6$ are as hereinbefore defined. Preference is given to the use of tetraalkylammonium salts, especially tetramethyl and tetraethylammonium salts. Good results have been obtained using n-butyl tetraethyl ammonium oxamide and t-butyl tetraethyl ammonium oxamide. In particular tetraethyl ammonium oxanilate has proven to be an excellent starting material for the process according to the present invention.

Another class of suitable starting materials comprises the compounds according to the general formula

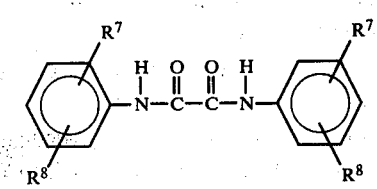

wherein $R^7$ and $R^8$ are as defined hereinbefore. Examples are oxanilide ($R^7=R^8=H$) and various substituted oxanilides such as 4,4'-dimethyloxanilide. the oxanilides can be prepared conveniently by reacting oxalic acid with the appropriate aniline.

It appears that the oxidative conversion of compounds having the group I in the structure can be carried out by various oxidative processes to obtain the appropriate isocyanates and/or the corresponding carbamates.

It has been found that compounds having at least one group I in the molecule wherein X represents the group OY wherein Y represents the group $NR^3R^4R^5R^6$ wherein $R^3$, $R^4$, $R^5$ and $R^6$ are as defined hereinbefore are conveniently oxidized electrochemically.

The electrochemical conversion of the compounds containing the group I in the structure can be carried out by methods known in the art. The conversion can be suitably carried out both in a two-compartment electrolysis cell as well as in a one-compartment electrolysis cell. Preference is given, however, to the use of a one-compartment electrolysis cell which obviates some major technical requirements inherent to the use of two-compartment cells, notably the lack of suitable membranes when aprotic solvents have to be used in the electrochemical process envisaged. The use of a one-compartment cell is highly advantageous provided the materials converted at the counter-electrode and their products do not substantially interfere with the reaction at the working electrode.

One-compartment cells which are especially suited for the electrochemical conversion comprise the so-called capillary gap cells. These cells can be used in batch-wise as well as in (semi)-continuous operations, and especially in continuous operations. Also modifications of the capillary gap cell such as the pump cell or cells like the trickle-tower cell can be used conveniently.

It will be clear that the starting materials containing the group I wherein X represents the group OY wherein Y represents the group $NR^3R^4R^5R^6$ also serve as electrolytes in the electrochemical conversion; additional supporting electrolytes known in the art can also be used (e.g., tetraalkylammonium tetrafluoroborates and -perchlorates).

The electrochemical conversion can be carried under potentiostatic or under galvanostatic conditions. In general, it has been found that better results can be obtained when the conversion is carried out under controlled current conditions. Various current densities can be employed in the process according to the present invention. It will be advantageous to employ relatively high current densities in order to achieve high use of electrolysis cell capacity depending on factors such as cost and source of electrical current, resistance of the reaction medium, heat dissipation problem and impact upon yields. Current densities of from 5–1000 milliamperes per square centimeter ($mA/cm^2$) can suitably be applied, preference being given to current densities of 15 $mA/cm^2$ and above.

The electrodes to be used in the electrochemical conversion can be of any electrode material which is relatively inert under the reaction conditions. Suitable anodes are various types of carbon and iron oxide although other materials (e.g., platinum, lead dioxide and other metal oxides) can be used as well. Cadmium, lead, platinum, mercury and mercurated lead are good cathodic materials although other materials can be used as well. Very good results can be obtained using a graphite anode and a platinum cathode.

The electrochemical conversion can be carried out in a wide range of temperatures. Temperatures in the range of from +120° C. to −30° C. can be suitably applied, preference being given to temperatures up to 60° C. It is sometimes found that temperatures below 0° C. are to be preferred from a selectivity point of view. Normally, good results are obtained when the electrochemical conversion is carried out at ambient temperature or slightly below.

The electrochemical conversion is normally carried out in the presence of a suitable solvent. Examples of suitable solvents comprise, for instance ethers, such as dimethoxyethane, diethylether, tetrahydrofuran, dioxane and macrocyclic ethers (e.g., represented by 1,4,7,10,13,16-hexaoxacyclooctadecane), chlorinated or fluorated hydrocarbons such as methylene dichloride and chloroform, nitriles such as acetonitrile, formamides such as dimethyl formamide, sulpholane and substituted sulpholanes, organic carbonates such as propylene carbonate, nitromethane, N-methyl-2-pyrrolidone and hexamethylphosphoric triamide. Also mixtures of solvents can be applied.

Since the electrochemical process requires the additional presence of protons, preference is given to the use of solvents which are capable of generating them. Also other proton sources can be used such as pyridinium hydrochloride and ammonium halides.

It should be noted that the electrochemical conversion can also be carried out in the presence of a solvent which is capable of reacting with the isocyanate product (or a precursor thereof). For instance, when the reaction is carried out in the presence of an alkanol, e.g., methanol or ethanol, the corresponding carbamate is formed rather than the free isocyanate. It may be advantageous because of the high reactivity of isocyanates as such to carry out the electrochemical conversion in an alkanol and to convert the carbamate obtained back into the isocyanate when required. Other solvents which could be used to trap temporarily the isocyanate product are secondary amines (which would lead to urea type derivatives) and fluorinated alkanols such as 2,2,2-trifluoroethanol. The use of alkanoic acids and/or alkanoic acid anhydrides (e.g. acetic acid and/or acetic acid anhydride) gives rise to the production of the corresponding acetanilides when the products aimed at were phenylisocyanate or derivatives thereof. Preference is given to a "solvent" system comprising acetonitrile, methylene dichloride and acetic acid anhydride and/or acetic acid.

It has also been found that the electrochemical conversion of compounds containing the group I wherein X represents the group OY wherein Y represents the group $NR^3R^4R^5R^6$ can be carried out in an indirect way by performing the conversion in the presence of compounds according to the general formula AD wherein D represents an anion which can be oxidized at the anode and the product formed thereof is capable of reacting with the starting material to produce the isocyanate and to reproduce the anion D. Normally the cation A will be of the general structure $NR^3R^4R^5R^6$ wherein $R^3$, $R^4$, $R^5$ and $R^6$ are as defined hereinbefore. Examples of suitable anions comprise the halogen anions chloride and bromide. Good results can be obtained using a tetraalkylammonium bromide such as tetramethylammonium bromide or tetrabutylammonium bromide as mediator.

It has further been found that compounds containing the group I wherein X represents the group OY or the group

wherein Y and Z are as defined hereinbefore can be converted oxidatively by treating them with an oxidizing agent. This method is especially suitable for compounds containing the group I wherein X rperesents the group OY wherein Y represents the group

such as oxanilides and derivatives thereof since two moles of isocyanate can be obtained from one molecule of starting material instead of only one molecule and a molecule of less valuable carbon dioxide.

Suitable oxidizing agents which can be used in the conversion of the starting materials as defined hereinbefore comprise chlorine, bromine, iodine as well as mixed halogen compounds. Also compounds like sulphuryl-chloride and the various hypohalides (e.g., sodium hypochlorite) can be used. Reference is also made to the various bleaching agents (e.g., calcium hypochlorite/calcium oxide) as well as to suitable organic halides such as N-bromo-succinimide and sodium p-toluene-sulfochloromide which is available under the trade name chloramine T.

Normally these oxidative conversions will be carried using methods known in the art. Suitable solvents comprise hydrocarbons and especially halogenated hydrocarbons (when free halogens or halogen compounds are used) as well as nitrobenzene. Examples of such solvents comprise methylene chloride, chloroform, carbon tetrachloride and dichloroethane. The use of mixed solvents is also possible. The oxidative conversions are generally carried out at room temperature and atmospheric pressure. But other temperatures and/or pressure may be used equally well.

The products obtained according to the process according to the present invention can be recovered by a variety of procedures known in the art depending on the particular type of product obtained.

The invention will now be illustrated by means of the following Examples.

EXAMPLE I

The electrochemical oxidation of tetraethylammonium oxanilate was carried out in an one-compartment cell (graphite anode, platinum cathode). The starting material was prepared by firstly reacting aniline and diethyloxalate to give ethyloxanilate which compound was then saponified with tetraethylammonium hydroxide; the yield was more than 90%.

(a) Tetraethylammonium oxanilide was electrolyzed using a solvent mixture containing acetonitrile, methylene chloride and acetic acid anhydride together with a small amount of acetic acid. After the theoretical amount of current had passed (2 Faradays per mole of tetraethylammonium oxanilide) phenyl isocyanate had been formed in 30% current yield.

(b) The experiment described in Example Ia was repeated but using 15 mmol of tetraethylammonium oxanilide in a mixture of acetic acid anhydride and acetic acid (50 ml, 2/1 v/v). Acetanilide was found in 60% current yield. In order to demonstrate that phenylisocyanate has been formed and was subsequently converted into acetanilide, two independent reactions were carried out: phenylisocyanate was reacted with acetic acid anhydride/acetic acid and did give acetanilide whereas tetraethylammonium oxanilide did not give any acetanilide when treated with acetic acid anhydride and acetic acid under otherwise similar reaction conditions.

(c) The experiment described in Example Ia was repeated but using methanol (75 ml) as the solvent, leading to phenylcarbamate as the predominant product. Two sets of experiments were carried out under controlled potential and under controlled current condition. The applied potential in the controlled potential condition was +1.6 V vs SCE. After the theoretically needed amount of electricity to convert 0.1 mol of tetraethylammonium oxanilide had been passed, it was found that the conversion of the starting material amounted to 77%. Phenyl carbamate had been formed in 49% chemical yield (38% current yield). A small amount of diphenylurea had also been formed. The experiment was also carried out under controlled current conditions (60 mA/cm$^2$). The conversion of tetraethylammonium oxanilide amounted to 73% and phenylcarbamate had been formed in 69% chemical yield (45% current yield). A small amount of diphenylurea had also been formed.

From these experiments it can be concluded that preference should be given to an experimental approach wherein the reaction is performed under constant current conditions. It was found that the amount of by-product diphenylurea obtained can be suppressed by the addition of an electrolyte like tetrabutylammonium tetrafluoroborate. However, the amount of product obtained also decreases at the same time.

(d) The experiment described in Example I, c, was repeated under galvanostatic conditions using an iron oxide ($Fe_3O_4$) anode. Phenyl carbamate could be obtained in 75% material yield.

EXAMPLE II

In order to demonstrate the indirect electrochemical oxidation of tetraethylammonium oxanilate, this compound was dissolved in acetonitrile in the presence of tetrabutylammonium bromide. The electrochemical formation of phenyl isocyanate occurred in small yield.

EXAMPLE III

The non-electrochemical oxidation of tetraethylammonium oxanilate was demonstrated by shaking a solution of this compound in methylene dichloride with molecular chlorine. The total amount of product was 13% and it contained a mixture of approximately equal amounts of phenyl isocyanate and chlorinated phenyl isocyanate. The experiment was repeated using the free acid, oxanilic acid, rather than the ammonium salt. Comparable results were obtained.

EXAMPLE IV n-Butyl tetraethylammonium oxamide was prepared as starting material for the electrochemical conversion into n-butyl isocyanate by reacting n-butyl amine, diethyloxalate and tetraethylammonium hydroxide in a similar way as described in Example Ia. The yield of n-butyl tetraethylammonium oxamide was 80%. This compound was then electrolysed under potentiostatic conditions at a graphite anode in a mixture of acetonitrile, dichloromethane, acetic acid anhydride and acetic acid. The desired product, n-butyl isocyanate was obtained in 11% yield (determined using gas-liquid chromatography).

EXAMPLE V n-Butyl tetraethylammonium oxamide was also converted into n-butyl isocyanate by reacting it with bromine in dichloromethane. n-Butyl isocyanate was obtained in 12% yield (determined using gas-liquid chromatography).

EXAMPLE VI t-Butyl tetraethylammonium oxamide (prepared as described in Example IV starting from t-butylamine) was converted into t-butyl isocyanate by shaking this compound in dichloromethane with bromine. The yield of t-butyl isocyanate amounted to 50% (determined using gas-liquid chromatography).

EXAMPLE VII

In order to demonstrate the feasibility of the process according to the present invention to prepare the di-carbamate of methylene-4,4'-diphenyldiisocyanate (MDI), the starting material methylene-4,4'-di(tetraethylammonium) oxanilide was prepared as follows: 4,4'-diamino-diphenylmethane was heated at 100° C.-130° C. for 5 hours with an excess of diethyloxalate. Methylene-4,4'-di(ethyloxanilide) was obtained in pure form in 95% yield with complete recovery of excess diethyloxalate. This compound was then saponified with potassium hydroxide or tetraethylammonium hydroxide to give the di-potassium and di-tetraethylammonium salts, respectively, in nearly quantitative yield.

(a) A clear solution of methylene-4,4'-di(tetraethylammonium) oxanilide in methanol/dichloromethane was oxidized at +1.6 V vs SCE using a graphite anode. Methylene-4,4'-diphenyldicarbamate was formed in 12% current yield.

(b) The experiment was repeated under galvanostatically controlled conditions. The experiment was performed in methanol at a current density of 33 mA/cm². The dicarbamate was obtained in 34% material yield (22% current yield).

EXAMPLE VIII

In order to demonstrate the indirect electrochemical oxidation of methylene-4,4'-dipotassium oxanilide, a suspension of this salt (5 mmol) in dry methanol was electrolyzed in the presence of 0.5 eq. tetraethylammonium bromide using a graphite anode and a platinum cathode at +1.6 V vs SCE. The desired dicarbamate was obtained in 6% current yield.

EXAMPLE IX

Methylene-4,4'-di(tetraethylammonium oxanilide) was converted into methylene-4,4'-diphenyldiisoyanate by reacting this compound with an equivalent amount of bromine in dichloromethane at room temperature. The yield of MDI amounted to 10% (determined using gas-liquid chromatography).

EXAMPLE X

The experiment described in Example VII a was repeated using toluene-2,4-di(tetraethylammonium oxanilide) as the starting material. This compound was obtained in 80% yield by heating 4-methyl-1,3-phenylene diamine with diethyloxalate and treating the product obtained with tetraethylammonium hydroxide. A clear solution of toluene-2,4-di(tetraethylammonium oxanilide) in methanol was electrolyzed under galvanostatically controlled conditions (graphite anode, platinum cathode, current density 33 mA/cm²). A small amount of the dicarbamate of TDI had been formed. Likewise toluene diisocyanate was also formed when toluene-2,4-di(tetraethylammonium oxanilide) was reacted with bromine in chloroform.

EXAMPLE XI

Oxanilide ($C_6H_5NHCO)_2$ was obtained in 80% yield by reacting aniline and oxalic acid under conventional conditions. Upon shaking oxanilide in methylene chloride with chlorine, phenyl isocyanate and chlorinated phenyl isocyanates were obtained (yield about 7%). Good results can be obtained using bleaching powder as the reactant.

We claim:

1. A process for the preparation of isocyanates and/or the corresponding carbamates containing at least one group having a structure selected from the group consisting of —N=C=O and

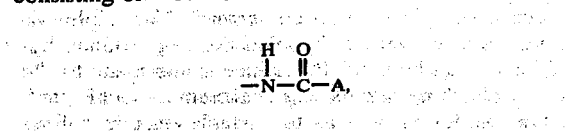

wherein A represents a group OB or $NR^1R^2$ wherein B represents an alkyl or aryl group which may or may not be substituted with one or more halogen atoms, alkyl or alkoxy groups and $R^1$ and $R^2$ which may be the same or different each represent a hydrogen atom or an alky or aryl group which may or may not be substituted with one or more halogen atoms, alkyl or alkoxy groups, which comprises oxidatively converting in a reaction zone as feed a compound selected from alkyl, aryl, alkaryl and aralkyl oxamic acids, salts thereof and oxanilides according to the general formula

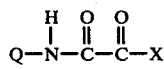

wherein Q represents a group selected from an alkyl group and an aryl group, which group may contain one or more substituents selected from a halogen atom or an alkyl or alkoxy group, a group

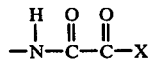

wherein X represents a group OY or

wherein Y represents a hydrogen atom, a metal ion or a group $NR^3R^4R^5R^6$ wherein each of $R^3$, $R^4$, $R^5$ and $R^6$ which may be the same or different, represent a hydrogen atom, an alkyl group having up to 8 carbon atoms, or an (alk)aryl group which may be substituted by one or more lower alkyl groups and Z represents an alkyl group or an aryl group which may be substituted by one or more substituents, or a group

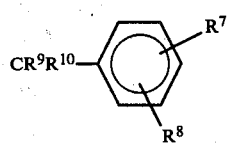

wherein $R^7$ and $R^8$ which may be the same or different each represent a hydrogen or halogen atom or an alkyl or alkoxy group, a group

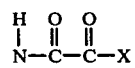

wherein X is as defined hereinbefore or a group

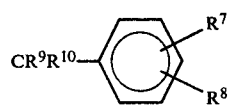

wherein $R^9$ and $R^{10}$ which may be the same or different each represent a hydrogen atom or an alkyl group; and separating the conversion products from said reaction zone.

2. A process according to claim 1 wherein the group Q represents a group having the structure

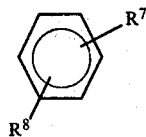

wherein $R^7$ and $R^8$ which may be the same or different each represent a hydrogen or halogen atom or an alkyl or alkoxy group, a group

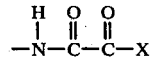

wherein X is as defined hereinbefore, or a group

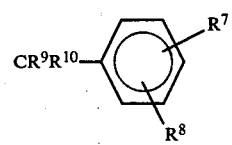

wherein $R^9$ and $R^{10}$ which may be the same or different each represent a hydrogen atom or an alkyl group.

3. A process according to claim 1 wherein the feed comprises a salt of an alkyloxamic acid having up to 12 carbon atoms, said salt being selected from the group consisting of ammonium, alkali metal and alkaline earth metal salts.

4. A process according to any one of claims 1, 2 or 3, wherein the oxidative conversion is conducted electrochemically.

5. A process according to claim 4, wherein in the reaction zone the electrochemical oxidation is carried out under controlled current conditions.

6. A process according to claim 4 or 5, wherein in the reaction zone the electrochemical oxidation is carried out in the presence of an additional electrolyte.

7. A process according to any one of claims 4–6, wherein the electrochemical oxidation is carried out at a temperature in the range of from +120° C. to −30° C.

8. A process according to any one of claims 4–7, wherein the electrochemical oxidation is carried out in the presence of a solvent which is capable of reacting with the isocyanate.

9. A process according to any one of claims 1, 2 or 3, wherin compounds having at least one group according to the structure

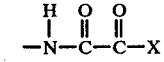

wherein X represents either a group OY, wherein Y is as defined hereinbefore, or a group NHZ wherein Z is as defined hereinbefore are oxidized using a halogen source as the oxidizing agent.

10. A process according to claim 9, wherein the oxidation is carried out using at least one oxidizing agent from the group consisting of chlorine, bromine, iodine, mixed halogen compounds, sulphurylchloride, hypohalites and bleaching agents.

11. A process according to claim 10, wherein the oxidation is carried out using at least one oxidizing agent selected from the group consisting of chlorine, bromine and calcium hypochlorite/calcium oxide.

* * * * *